United States Patent
Konno et al.

(10) Patent No.: US 8,029,513 B2
(45) Date of Patent: Oct. 4, 2011

(54) TIGHTLY BINDING DEVICE FOR BONE JOINING CABLE

(75) Inventors: Tomeo Konno, Chiba (JP); Shinetsu Kudo, Chiba (JP); Noritoshi Yamaguchi, Osaka (JP); Yasuyuki Hitomi, Kyoto (JP)

(73) Assignee: Alfresa Pharma Corporation, Osaka-Shi (JP)

( * ) Notice: Subject to any disclaimer, the term of this patent is extended or adjusted under 35 U.S.C. 154(b) by 1005 days.

(21) Appl. No.: 11/913,364

(22) PCT Filed: Apr. 28, 2006

(86) PCT No.: PCT/JP2006/309005
§ 371 (c)(1),
(2), (4) Date: Nov. 1, 2007

(87) PCT Pub. No.: WO2006/118259
PCT Pub. Date: Nov. 9, 2006

(65) Prior Publication Data
US 2009/0082821 A1      Mar. 26, 2009

(30) Foreign Application Priority Data
May 2, 2005    (JP) .............................. P2005-133906

(51) Int. Cl.
*A61B 17/58* (2006.01)
*A61B 17/60* (2006.01)
*A61F 2/00* (2006.01)
(52) U.S. Cl. ........................................ 606/103; 606/74
(58) Field of Classification Search ................ 606/86 R, 606/74, 103, 105
See application file for complete search history.

(56) References Cited

U.S. PATENT DOCUMENTS
1,347,579 A * 7/1920 Henrikson .................... 81/9.3
4,966,600 A * 10/1990 Songer et al. ................. 606/74
(Continued)

FOREIGN PATENT DOCUMENTS
JP         35-12766         6/1960
(Continued)

OTHER PUBLICATIONS

Alfresa Pharma Corp., 'Teiketsu Hojo Kigu Taitingu Gan [MH]' Catalog, Oct. 2004, full text; all drawings.
(Continued)

*Primary Examiner* — Eduardo C Robert
*Assistant Examiner* — Ellen C Hammond
(74) *Attorney, Agent, or Firm* — Millen, White, Zelano, Branigan, P.C.

(57) ABSTRACT

A bone-tying cable tightening device with improved easiness of handling of is disclosed. The device comprises a grip portion, a rod-like member extending forward, a knot supporter at the tip, a cable holder to grip and hold the tow arms together, and a sliding block mounted around the rod-like member and connected to a puller and an operation lever to drive the puller. The knot supporter supports two arms that can be hooked away from each other and laterally above the rod-like member, the cable holder is made up of a longitudinal through groove a locking recess which extends, at the end of the through groove, and a backward biased locking member which is provided movably back and forth behind the locking recess on the upper side of the sliding block made so that its forward movement is blocked when it fits in the locking recess.

26 Claims, 13 Drawing Sheets

U.S. PATENT DOCUMENTS

| | | | |
|---|---|---|---|
| 5,312,410 A | 5/1994 | Miller et al. | |
| 5,395,374 A | 3/1995 | Miller et al. | |
| 5,899,921 A * | 5/1999 | Caspari et al. | 606/232 |
| 6,752,810 B1 * | 6/2004 | Gao et al. | 606/103 |
| 2010/0087872 A1 * | 4/2010 | Morihara et al. | 606/300 |

FOREIGN PATENT DOCUMENTS

| | | |
|---|---|---|
| JP | 3074205 | 12/1993 |
| JP | 08-504119 | 5/1996 |
| JP | 09-502112 | 3/1997 |
| WO | WO 94/13229 | 6/1994 |
| WO | WO 95/06438 | 3/1995 |

OTHER PUBLICATIONS

Alfresa Pharma Corp., 'Teiketsu Hojo Kigu Taitingu Gan [NTG]' Catalog, Oct. 2004, full text; all drawings.

Patent Abstracts of Japan, publication No. 05-317332, Dec. 3, 1993.

* cited by examiner

TIGHTLY BINDING DEVICE FOR BONE JOINING CABLE

TECHNICAL FIELD

The present invention relates to a bone-tying cable tightening device for tightening bone-tying cables, which are used to firmly tie bones of affected part of the body together and keep holding them so as to allow them to fuse and unite with each other, with a strength of force required to keep them held together in bone surgeries for treatment of bone fracture or repositioning and fixation of bones, and the like.

BACKGROUND ART

In bone surgeries such as those for effecting fusion of bones (i.e., fusion and unification) after bone fracture, e.g., fusion of repositioned bones after spinal fracture, or following bone grafting, it is necessary that the relevant bones be kept tightly held together until their fusion is accomplished lest they should be displaced. In order to keep holding them together, steel wires have long been used, along with, depending on a given situation, a variety of devices such as metal rods, hooks, bolts (pedicle screws) and the like. From a standpoint, however, of avoiding the risk of spinal cord injury caused by the tips of the steel wires that could be created by fracturing during or after a spine surgery, use of metal fiber-made cables or cables made of high-strength synthetic fibers, such as ultra-high molecular weight polyethylene (referred to collectively as "bone-tying cables" in the present invention), has been becoming popular instead of steal wires.

In a surgery employing bone-tying cables, as FIG. 1 schematically illustrates the procedure of tying according to a typical manner using one of the above-mentioned cables made of synthetic fibers, bones to be held together (shown as round bars) are first tied with a loop of a bone-tying cable (together, if necessary, with a rod, a hook or the like as a splint), and then, (1) while the knot (provisional knot) shown in FIG. 1(*f*) being supported, the two arms of the cable extending from it are held together and pulled tightly so that the size of the loop is reduced and the bones are fastened to each other, and, when the tension of the loop has been increased up to a required level, the knot is immobilized in the situation with, e.g., an adhesive or an attachment, or (2) a provisional knot is formed from the situation depicted in FIG. 1(*g*) by pulling the two arms by hand in the directions indicated with the arrowheads, and, the two arms of the cable extending therefrom are then pulled firmly in both lateral directions, so that the size of the loop is reduced and the bones are fastened to each other, and, when the tension of the loop has been increased up to a required level, the knot is immobilized, with the tension being retained, by means of additional knots or an adhesive or the like, as required to prevent it from slipping. The above fastening process using the bone-tying cable must be a process in which a strong tension (e.g., 5-10 kgf) is created in the cable forming the loop. In order to overcome the frictional force between the fibers of the cable within the provisional knot, thereby causing them to slip with one another and thus reducing the size of the loop to achieve such a strong tension in it, the two arms extending from the provisional knot must be pulled with a force which will creates a greater tension in both of them. A device to enable this is known and has been produced by the applicant of the present application, with which the two arms of the bone-tying cable extending from the provisional knot are separately held and pulled (see Patent Document 1). With this device, fastening is performed by first putting the tip of the device against the provisional knot, then holding the two arms of the cable extending from the provisional knot separately with different structures at different positions, and pulling them rearward. With this device, however, unless the forces with which to pull the two arms are constantly adjusted to be equal, the provisional knot is likely to slip away from the tip of the device. Thus there was a room with this device for some improvement for easiness of operation.

Devices improved in this respect have been developed by the applicant of the present invention, which devices are; a bone-tying cable tightening device which is so made as to allow pulling the both arms of the bone-tying cable extending from a knot together as a bundle through a slit provided at the tip of the device (see Non-Patent Document 1), and a bone-tying cable tightening device which is so made as to once separate the cable's two arms in lateral directions and then hold and pull them together as a bundle, and which includes a trigger coupled with a ratchet mechanism enabling easier tightening of the cable, and is provided with a tension-adjusting mechanism for adjusting the tension applied to the cable (see FIGS. 2, 4, 5 and Non-Patent Document 2). And both are used in medical facilities across the country under the commercial names of "Tighting Gun [MH]" and "Tighting Gun [NTG], respectively. The latter device, for example, is provided, at the tip of its rod-like member 4, which extends forward from a grip portion 3, with a pair of projections as a knot-supporting means 5 extending in one lateral direction (on the left side relative to the forward direction, i.e., on the near side in the figures), and includes a sliding block 6 which is mounted, slidably in the longitudinal direction, around the rod-like member 4, wherein the sliding block 6 includes a guide projection 7 projecting in a lateral direction (on the left side relative to the forward direction, i.e., on the near side in the figures) and having a smooth cylindrical side face. On the sliding block 6 and closely above the guide projection 7, a pair of projections 8, 9 projecting also in the lateral direction (projection 8 is fused to and united with the guide projection 7) are provided, defining between then a space 10 through which the cable is allowed to pass in the vertical direction. In its cross section, the space 10 widens upward in a V-shape manner, and, to match the shape of the cross section, a transverse groove 11, which also widens upward, is defined in the upper part of the sliding block 6. Above the sliding block 6, a bar-like locking member 12 is supported by a pivotable arm 13, and the locking member 12 can fit with its side faces between the pair of projections 8, 9 and also within the transverse groove 11. The arm 13 is journaled on the sliding block 6 on the side opposite to the knot-supporting means 5 (on the other side of the sliding block 6 in the figures), and is biased upward with a spring so that the locking member 12 may be brought away from the space 10 and the transverse groove 11. In the grip portion 3, there is provided a drum, which is rotated stepwise in a fixed direction by a ratchet mechanism in response to pulling of a trigger 14. A pull cable 15, which is secured at one end of it to the drum, is secured at its other end to the rear face of the sliding block 6, and the device is so made that when the trigger 14 is repeatedly pulled, the sliding block 6 is forced to slide and retreat along the rod-like member 4. Further, the rod-like member 4 is supported by the grip portion 3 in such a manner that a rearward slide of the rod-like member 4 is allowed, with its rear end being connected to a tension-adjusting knob 17 which is equipped with a screw mechanism.

This device is used in the manner as schematically illustrated in FIGS. 3 and 4. Briefly, the device is held with a dominant hand, and while putting the knot-supporting means 5, which projects in the lateral direction from the rod-like member 4, against the provisional knot 21 of the cable which ties the bones 20 to be fastened. The two arms 22, 23 of the cable are separately hooked by the other hand on the upper and lower sides of the knot-supporting means 5, and then the both ends of the arms are held together and pulled in the proximal direction along the side face of the rod-like member 4 (FIG. 3(h)). Then the arms of the cable are hooked on the guide projection 7 to make a turn upward while being kept tense, and then, after being passed through the space 10 between the pair of projections 8, 9, they are hooked on the locking member 12, which is lifted above the sliding block 6 (FIG. 3(i)), and wound once about it (FIG. 3(j)). By pulling the trigger 14 a few times to pull the pull cable 15 and thereby making the sliding block to retreat, the locking member 12 is pulled down into the space 10 between the projections 8, 9 and also into the transverse groove 11. Thus, the two arms 22, 23 of the cable wound about the locking member 12 are securely held in position clamped between the V-shaped slopes of the space 10 and the both side walls of the transverse groove 11 and the locking member 12. Then, by repeated pulling of the trigger 14, the sliding block 6 gradually retreats in the rearward direction, and the two arms 22, 23 of the cable are pulled tightly, which, causing the cable to slip within the provisional knot, reduces the size of the loop and thereby firmly tie the bones to be fastened. At the very moment when the tension goes up beyond a predetermined level which has been set with the tension-adjusting knob 17, the rearward pressure from the sliding block 6, which is received by the rod-like member 4 at the knot-supporting means 5 via the two arms 22, 23 of the cable, overcomes the repulsive force of the spring which has been adjusted with the tension-adjusting knob 17, and the rod-like member 4 thereby slides slightly rearward for the first time. This movement is detected, e.g., through a window 25. Thus, after it is known that the predetermined strength of tension is achieved, a release lever 26 is moved to release the ratchet, thereby allowing the sliding block 6 to slide forward and loosen the two arms 22, 23 of the cable, which are then removed from the device. Though, in this situation, the knot is tightly fastened and will not easily return to its previous state, it is also possible to add one or more extra knots, to bond the knot with an adhesive, or to fix the knot with an attachment, for securer fixation of the knot.

While this device enables one to fasten target bones with required strength of tension and thus is widely used, it still have a room for improvement with respect to easiness of operation. For the device is unstable at the tip and somewhat readily fluctuates sideways and back and forth due to unsteadiness of the hand during the process in which the two arms of the cable extending from a provisional knot are held together and hooked on the guide projection 7, made to turn upward and then wound around the locking member 12. Therefore, in the case of a surgeon who is not accustomed to the handling of the device, the knot-supporting means 5 sometimes moves away from the provisional knot unless he handles the device with sufficient care, thereby making it necessary to carry out the process once again from the step where the tip of the device is put against the provisional knot. This has sometimes been troublesome for surgeons, who have to smoothly perform the surgery, in which there are often cases where fastening must be given at multiple points. Therefore, a device which is easier to handle has been needed with which factors causing to such unsteadiness of hand are reduced.

[Patent Document 1] Japanese Patent No. 3074205

[Non-patent Document 1] Pamphlet of "Tighting Gun [MH]", Medical Device Approval No. 12BZ0286, Alfresa Pharma Corporation, Revised in October, 2004.

[Non-patent Document 2] Pamphlet of "Tighting Gun [NTG]", Medical Device Approval No. 12BZ0286, Alfresa Pharma Corporation, Revised in October, 2004.

DISCLOSURE OF INVENTION

The Problem to be Solved by the Invention

Against the above mentioned background, the inventors of the present invention, as a result of studies, found that the chief causes of the unsteadiness of hand reside in: (i) that an excess transverse force is applied to the rod-like member 4 as the user turns the direction of the cable upward by hooking it on the guide projection 7 on the sliding block 6, for the bone-tying cable must be kept tense, and it is relatively difficult for him, until he has got used to the device, to wind the bone-tying cable about the locking member 12 while keeping subtle balance against this transverse force; and (ii) that the process of hooking the bone-tying cable on the guide projection 7, which projects in the lateral direction from the sliding block, and passing it through the groove between the projections 8, 9 and then winding it about the locking member 12, is generally to be done while viewing the side face of the device obliquely from behind, thus often shielding from view the tip of the device by the hand which is holding the cable, and further (iii) that the substantial distance in the field of view between the position of the locking member 12, about which the cable is wound, and position of the tip of the device, makes it difficult for the user to pay attention evenly to them both, likely rendering the holding of the position of the knot-supporting means 5 at the tip less attended. The objective of the present invention is to provide an improved bone-tying cable tightening device with which the above problems have been solved.

Means to Solve the Problem

As a result of studies for the above objective, whereas with the conventional devices, due to the knot-supporting means, i.e., the projections 5 at its tip of the devices, projecting in the lateral direction relative to the rod-like member 4, the two arms of the bone-tying cable extending from the provisional knot are divided into upper and lower ones relative to the longitudinal axis of the rod-like member 4 and thus held sideways relative to it, therefore making those devices of a structure according to which it is handled with its central plane being kept in parallel to the plane of the loop of the bone-tying cable, the inventors sought to make a device which would allow one to use it with its central plane being held perpendicular to the plane of the loop, and to evenly pull the right and left arms of the bone-tying cable relative to the device, and with which the bone-tying cable can be handled as far as possible along the straight line from the provisional knot to the point where the cable is wound about the locking member. The inventors thus found a mechanism suitable to this purpose, and, having confirmed that it has solved the above-mentioned problems, completed the present invention.

Thus, the present invention provides what follows.

1. A bone-tying cable tightening device for firmly tying objects to be tied, by pulling the two arms extending from the knot of a cable tying the objects to be tied, comprising a grip portion to be held with a hand, a rod-like member which extends forward from the grip portion, a knot-supporting means provided at the tip of the rod-like member to support the knot when the two arms are pulled, a sliding block mounted around the rod-like member in a longitudinally slidable fashion, which sliding block is provided with a cable-holding means to grip and hold the two arms together and is connected, via a tension transmitter means, to a pulling means installed in the grip portion, and an operation lever provided in the grip portion to drive the pulling means, wherein the knot-supporting means is of a structure which defines, above the rod-like member, (1) supporting faces on both sides thereof of which the two arms can be hooked away from each other and laterally relative to the longitudinal axis of the rod-like member, and/or (2) a slit or bore through which the two arms can be passed, and wherein the cable-holding means provided to the sliding block comprises (a) a longitudinal through groove defined in the upper part of the sliding block, (b) a locking recess which extends, at the rear end of the through groove, either transversing the through groove in the cross section thereof or including the cross section of the through groove along the central axis thereof, and whose width in the cross section thereof widens in the rearward direction, (c) a backward biased locking member about which the two arms are to be wound, and which is provided movably back and forth behind the locking recess on the upper side of the sliding block and so made that the forward movement thereof is blocked when it proceeds in the locking recess and abuts, with the side faces thereof, on the same.

2. The bone-tying cable tightening device as defined in 1 above, wherein the locking recess extends covering the cross section of the through groove along the central axis thereof.

3. The bone-tying cable tightening device as defined in 2 above, wherein the locking member is attached to an arm which is installed, pivotably about a vertical axis, on the sliding block and on the same side as the knot-supporting means relative to the rod-like member.

4. The bone-tying cable tightening device as defined in 3 above, wherein the locking recess defines in the edge thereof an indentation which can accommodate the arm as the locking member fits in the locking recess.

5. The bone-tying cable tightening device as defined in 3 above, wherein the arm has a contour which evades the edge of the locking recess so that the arm may avoid interference with the edge of the locking recess as the locking member fits in the locking recess.

6. The bone-tying cable tightening device as defined in one of 3 to 5 above, wherein the arm is journaled on the sliding block.

7. The bone-tying cable tightening device as defined in 6 above, wherein the backward bias of the locking member is given by a spring installed around the pivotal shaft of the arm journaled on the sliding block.

8. The bone-tying cable tightening device as defined in 2 above, wherein the locking member is installed at the tips of the second arms of a five-link chain mechanism which consists of a pair of first lateral arms of equal length which are installed, on the same side as the knot-supporting means relative to the rod-like member, pivotably about vertical axes on both lateral sides of the sliding block and extending diagonally in lateral directions, respectively, and a pair of second lateral arms of equal length which are attached, pivotably about vertical axes, to one or the other of the pair of first lateral arms at the tips thereof, and extends diagonally in inward directions therefrom, respectively, the tips of the pair of second arms being connected pivotably with each other about a vertical axis.

9. The bone-tying cable tightening device as defined in 8 above, wherein the pair of first arms are journaled on the sliding block.

10. The bone-tying cable tightening device as defined in 9 above, wherein the backward bias of the locking member is given by a spring installed around at least one of the pivotal shafts of the pair of first arms journaled on the sliding block.

11. The bone-tying cable tightening device as defined in 2 above, wherein the locking member is installed on a sliding member which is mounted on, and slidably back and forth relative to, the sliding block.

12. The bone-tying cable tightening device as defined in 11 above, wherein the sliding member slides along a sliding guide formed in the sliding block and to which part of the sliding member fits.

13. The bone-tying cable tightening device as defined in 12 above, wherein the backward bias of the locking member given by a spring installed in the sliding guide in association with the sliding member.

14. The bone-tying cable tightening device as defined in 1 above, wherein the locking recess extends transversing the through groove in the cross section thereof.

15. The bone-tying cable tightening device as defined in 14 above, wherein the locking member is mounted on an arm which is installed, pivotably about a horizontal axis, on a lateral side of the sliding block.

16. The bone-tying cable tightening device as defined in 15 above, wherein the arm extends generally in the upward direction from the lateral side of the sliding block, and the locking member extends from the tip of the arm, in the rear of the locking recess and in parallel to the same.

17. The bone-tying cable tightening device as defined in 15 above, wherein the arm extends generally in the upward direction separately from the both lateral sides of the sliding block, respectively, and then inward above the sliding block to unite into one body, and again generally in the upward direction, and at the tip of the arm the locking member is attached.

18. The bone-tying cable tightening device as defined in one of 15 to 17 above, wherein the arm is journaled on the sliding block.

19. The bone-tying cable tightening device as defined in 18 above, wherein the backward bias of the locking member is given by a spring installed around the pivotal shaft of the arm journaled on the sliding block.

20. The bone-tying cable tightening device as defined in 14 above, wherein the locking member is installed on a sliding member which is mounted on the sliding block, slidably back and forth relative thereto.

21. The bone-tying cable tightening device as defined in 20 above, wherein the sliding member slides along a sliding guide which is formed in the sliding block and to which part of the sliding member fits.

22. The bone-tying cable tightening device as defined in 21 above, wherein the backward bias of the locking member is given by a spring installed in the sliding guide in association with the sliding member.

23. The bone-tying cable tightening device as defined in one of 1 to 22 above, wherein the width of the locking recess in the cross section thereof widens in a V-shaped fashion in the rearward direction.

24. The bone-tying cable tightening device as defined in one of 1 to 22 above, wherein the width of the locking recess in the cross section thereof widens in a circular arc-like fashion in the rearward direction.

The Effect of the Invention

With the present invention as defined above, there is no more need for a change in the direction of the bundle of the two arms of the bone-tying cable into the transverse direction during the process of leading the bone-tying cable up to the locking member, and this eliminates the transverse force which conventionally must have been applied before winding of the cable; and the tip of the device will be no more shielded from view by the hand during the process of winding the cable; and further, the cable now runs substantially straight between the tip of the device and the locking member during the manipulation of the device, which makes it easier for the user to pay even attention to both of them simultaneously. As a result, with the present invention, the process up to winding the cable about the locking member is made much easier compared with the prior devices. Further, while the conventional devices are basically to be handled in the operator's right hand, the device of the present invention, which is bilaterally symmetrical from the practical point of view, can be handled exactly alike either with right or left hand, and therefore has an advantage that it is free of dominant-hand dependency.

EXPLANATION OF SIGNS

Figure 1:
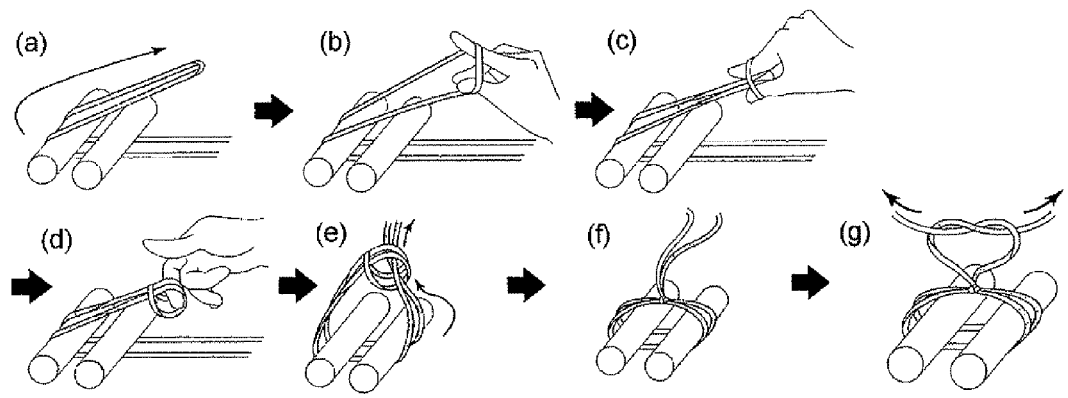
FIG. 1 is a schematic diagram showing the manner of encircling bones in a bone-tying cable and giving a provisional knot to it.
Figure 2:
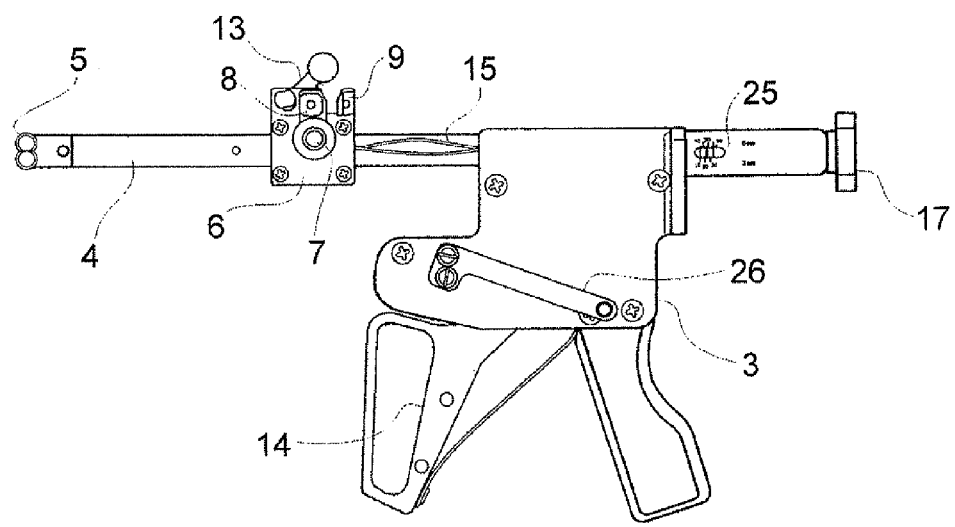
FIG. 2 illustrates a side view of the bone-tying cable tightening device of a conventional type.

3=grip portion
4=rod-like member
5=knot-supporting means
6=sliding block
7=guide projection
8=projection
9=projection
10=space
11=transverse groove
12=locking member
13=arm
14=trigger
15=pull cable
17=tension-adjusting knob
33=grip portion
34=rod-like member
35=projection
36=sliding block
37=pull cable
40=operation lever
42=through groove
44=locking recess
46=locking member
48=arm
50=indentation
55=rotary drum
57=gear
59=gear
61=ratchet wheel
63=leaf spring
65=feed pawl
67=tip of feed pawl
69=pin
71=one-way detent
73=release lever
75=tension-adjusting knob
79=cylindrical member
81=spacer
83=coil spring
85=window
87=scale marks 90=bone
91=bone
93=loop
94=arm
95=arm
100=sliding block
102=first arm
103=first arm
104=second arm
105=second arm
106=indentation
110=sliding block
112=basal plate
114=coil spring
120=sliding block
122=arm
124=locking member
130=through groove
132=locking recess
134=projection
136=sliding block
138=arm
140=locking member
150=sliding block
152=basal plate
154=coil spring
156=locking member
160=through groove
162=locking recess
170=cylindrical portion
S=slit

BEST MODE FOR CARRYING OUT THE INVENTION

In the present invention, there is no particular limitation as to the shape and size of the grip portion insofar as it is easy to grip and handle. The rod-like member extending from the grip portion may be fixed to the grip portion, or it may be attached in such a manner that it can retreat by sliding when pulled with a force over a predetermined strength. There is no particular limitation as to the length and thickness of the rod-like member. As to length, it is enough that the rod-like member reserves a space for the sliding block to retreat by at least about several cm. And as to thickness, it is enough that the rod-like member endures a longitudinal compressive force of several dozen kgf. The shape of its cross section may also be as desired as long as it allows sliding motion of the sliding block. It is convenient to provide the rod-like portion with a cross section of, for example, rectangular.

The knot-supporting means is a means for supporting the provisional knot against the tension as the two arms of the bone-tying cable extending from the provisional knot are pulled in the rearward direction. The knot-supporting means may be (1) of a type according to which the provisional knot is placed in the middle of the knot-supporting means and then the two arms of the cable, which are separated in both lateral directions, are pulled backward, or (2) of a type which has a bore or slit of a width that allows to pass and pull the two arms of the cable backward through it (but not allowing to pass the provisional knot of the cable through it), or further (3) of a type in which the former two types are combined together. Specifically, a knot-supporting means of type (1) may be, for example, in the form of a projection, or a pair of projections placed adjacent to each other and in bilaterally symmetrical arrangement, at the tip of the rod-like member, or may be provided as a portion which is formed by bending the tip of the rod-like member upward. In such cases, since the arms of the cable are drawn along the side faces of it, the knot-supporting member preferably has smooth surfaces at least on its side faces supporting the cable, in order to avoid excess friction. Further, it is preferred that the knot-supporting member has on each of its side faces a recessed area (e.g., a recessed area conforming to a saddleback surface), in order to prevent the two arms of the cable from slipping off upward from the knot-supporting means as the two arms of the cable are pulled along the side faces of the knot-supporting means. Furthermore, specific examples of type (2) include a pair of projections on the rod-like member so arranged as to define a slit between them (of whatever longitudinal depth) which allows the cable to be passed in the backward direction, and a cylindrical or an annular structure defining a bore facing in the longitudinal direction. Specific examples of a type in which types (1) and (2) are combined together include a pair of projections of type (1) the space between which is made as a slot of type (2), and a single projection of type (1) which defines a through bore in the longitudinal direction.

As the through groove is defined in the sliding block for the purpose of receiving sideways the two arms of the bone-tying cable pulled in a bundle, what is required for the through groove is that it has a sufficient width and depth to let the cable's two arms pass through within it. What is required for the locking recess is that it blocks the forward movement of the locking member that has fit in it, by abutting with its side faces on the side faces of the locking member. Therefore, the shape and size of it may be determined to meet this purpose as desired in accordance with the size of the locking member. Though it is convenient to give the locking recess a V-shaped cross section, it may also be possible to provide it as a groove having a round cross section, e.g., arc-like one, in which case the dimensions of the locking recess may be determined so that the two cable's arms wound about the locking member may be clamped between the locking member and sloped part on both sides of the of the locking recess in its arc-like cross section. Regardless of whether it is V-shaped or of arc-like in its cross section, the slope of the surfaces between which the cable is clamped and locked is preferably not less than 45 degree, more preferable not less than 55 degree, still more preferably not less than 60 degree, relative to a plane perpendicular to the direction in which the cable is pulled. In addition, the side faces of the locking member or the surface of the locking recess, or both of them, may have been subjected to a surface roughening process by, e.g., giving fine notches in them to create uneven surfaces, in order to increase their friction with the cable and achieve securer locking.

The locking recess may extend covering the cross section of, and along its central axis of the through groove in the sliding block, or it may extend transversing cross section of the through groove. In the former case, the basal portion of the locking recess is penetrated by the cross section of the through groove, and therefore the locking recess has only the faces left on both sides, which take part in engagement. In the case where the locking recess is given so that it transverse the through groove, the locking recess, though divided around its center by the cross section of the through groove, holds its intact shape in the remaining potion of it.

The locking member is oriented in parallel to the direction in which the locking recess extends. The locking member is attached, on the same side as the knot-supporting means relative to the rod-like member, to an arm which is installed, e.g., pivotably about a vertical axis, on the sliding block, and thus can come into and out of the locking recess from behind, moving along a circular orbit in a horizontal plane according to the swing of the arm. In this case, the arm may be given, on the side opposing to the edge of the locking recess, a contour having a recess into which the edge of the locking recess is received, by, e.g., bending the arm into the from of a hook, in order to avoid interference of the arm with the edge of the locking recess. Instead, an indentation may be given to the edge of the locking groove by removing part of it so that the arm can be received therein.

The above-mentioned arm may be journaled on the sliding block via a shaft member pivotably attached to the sliding block. The backward bias of the locking member (therefore or the arm) may be given by placing a spring around the shaft member within the sliding block.

In an arrangement which substitutes for the one-arm arrangement, the locking member may be installed at the tip of a five-link chain which is made including the sliding block. Namely, the locking member is installed at the tips of the second arms of a five-link chain mechanism which consists of a pair of first lateral arms of equal length which are installed, on the same side as the knot-supporting means relative to the rod-like member, pivotably about vertical axes generally symmetrically on both lateral sides of the sliding block and extending diagonally in lateral directions, respectively, and a pair of second lateral arms of equal length which are symmetrically attached, pivotably about vertical axes, to one or the other of the pair of first lateral arms at the tips thereof, and extends diagonally in inward directions therefrom, respectively, the tips of the pair of second arms being connected pivotably with each other about a vertical axis. This arrangement is that of a pantograph. According to this, the locking member moves along a straight liner, not along an arc, and comes to fit in the locking recess. In this arrangement, the proximal ends of the pair of first arms may be journaled on the sliding block via corresponding shaft members pivotably installed in the sliding block, and the backward bias of the locking member may be given by a spring or springs installed around one or the both of the shaft members in the sliding block.

Instead of these single-arm and multiple-arms arrangements, it is also possible to employ a sliding member, e.g. a plate-like member, which is mounted on the sliding block, slidably back and forth relative to it, on which the locking member is installed, and which is biased backward by a spring. For the back-and-forth sliding of the sliding member, a guide (sliding guide) may be provided on the sliding block. A sliding guide may, for example, consist of guide bores which receives, slidably in the longitudinal direction, a front and rear parts of the sliding member, respectively; or of a pair of projections, each having an L-shaped cross section, which slidably hold between them the sliding member on both sides thereof, and projections provided in front of and behind the sliding member, respectively, to confine its longitudinal motion within a predetermined range. A spring which biases the sliding member (therefore the locking member) backward may, for example, be installed within one of the guide bores, or between one of the said projections (e.g., the projection in the rear) and the sliding member.

In the case where the locking recess extends transversing the cross section of the longitudinal through groove, the locking member which is to fit in the locking recess also is positioned in the transverse direction accordingly. In this case, too, the back-and-forth motion of the locking member may be allowed either by placing it on an arm pivotably installed on the sliding block, or by placing it on a sliding member slidably installed on the sliding block. Specifically, for example, the locking member may be attached, in the rear of and in parallel to the locking recess, to the tip of an arm which is installed pivotably about a horizontal axis on a lateral side of the sliding block, or it may be attached, in the rear of and in parallel to the locking recess, to the tip of an arm which arm, after first extending separately from the both lateral sides of the sliding block, generally in the upward direction in a vertical plain, respectively, extends inward, above the sliding block, to unite into one body in the middle, and again extends generally in the upward direction. Employment of one of such arrangements allows the locking member to fit in the locking recess, following the movement in the longitudinal direction in an orbit, which is either circular or straight. A method for biasing the locking member backward may be the same as described above with regard to a vertical locking member.

There is no particular limitation regarding the specific structure of the grip portion. The grip potion may be provided with a cable winding means, such as a drum which is rotated stepwise in a fixed direction (directly, or via a separate convenient mechanism such as gears) by a ratchet mechanism in response to pulling of an operation lever which is associated with it, with one end of the pull cable being secured to the cable winding means and the other end to the back face of the sliding block. The cable winding means may be built so that, it may rotate as the operation lever is repeatedly pulled, thereby pulling the cable backward, and then causing the sliding block to slide backward along the rod-like member. Further, the rod-like member may be supported by the grip portion in such a manner that the former is allowed to slide backward. In this case, an arrangement is applicable in which the proximal end of the rod-like member rests on one end of a spring (e.g., a coil spring) installed in the grip portion, so that as the sliding block is pulled backward, the rod-like member, also to which the backward pulling force is applied via the bone-tying cable held by the sliding block, starts to retreat just when the strength of the pulling force rises beyond a predetermined level. By employing such an arrangement, the device is made so that it can inform the surgeon when the tension has reached the predetermined level. The strength of the tension at which the rod-like member starts to retreat may be set as desired, by confining the spring, which lies abutting on the rear end of the rod-like member, to an already compressed condition in which a repulsive force equals to the predetermined tension is generated within the spring. To do this, for example, the portion of the grip member in which the spring is installed may be built in such a manner that the spring may be inserted in a frame within which it is compressed and its allowable maximal length restricted, with the maximal length of the frame being adjustable with a screw mechanism.

Though the device of the present invention is preferably made of metal, it is also allowed to partly employ other materials such as heat-resistant resins, ceramics and the like, as far as they have enough strength to stand the above-mentioned compressive force, and at the same time, endure repeated heat sterilization before and after their use in surgical operations.

EXAMPLES

Though the present invention is described in further detail below with reference to examples, it is not intended that the present invention be restricted to those examples.

Example 1

FIGS. 6-10 shows a side view, a plan view, a front view, a back view and an enlarged partial view obliquely from behind, respectively, of an example of bone-tying cable tightening device 31 of the present invention. In these figures, 33 indicates a grip portion, from the front of which extends forward a rod-like member 34. Although the device will take a variety of postures in actual use of it, each direction relative to the device, i.e., upward, downward, rightward, leftward, forward or backward direction, will be defined in these figures, with the device being held so that the longitudinal direction of the rod-like member 34 extends horizontally, its tip pointing ahead, and the plane of symmetry of the grip portion 33 (which is bilaterally symmetrical as a whole) being held vertical, for convenience of description as well as understanding of the structure. The rod-like member 34 is supported by the grip portion 33 in such a manner that the former is allowed to slide backward, but is staying in the position as depicted in the figures, by being strongly biased from behind as will be mentioned later. The rod-like member 34 has at its tip a pair of projections 35 which, being bilaterally arranged with each other, extend upward. The pair of projections 35 has smooth side faces, recessed in their center and conforming to saddle-back surfaces, and function to support the provisional knot, when a bone-tying cable is being tightened. A slit "S" is defined between the pair of projections 35.

Around the rod-like member 34 is slidably fit a sliding block 36, to the rear part of which is secured an end of a pull cable 37 made of metal, which extends through the front face of the grip portion 33. The other end of the pull cable 37 is secured to a rotary drum provided inside of the grip portion 33, and the rotary drum is so made that it is rotated stepwise in a fixed direction through a ratchet mechanism operated by an operation lever 40, which extends from the grip portion 33 in the form of a trigger. The pull cable 37, which is secured at its one end to the rotary drum, therefore, is pulled backward when the rotary drum rotates by being driven by pulling the operation lever 40, and it then pulls backward the sliding block 36, to which the front end of it is secured.

The sliding block 36 defines in its upper part a longitudinal through groove 42 (see FIGS. 7 and 10), and the through groove 42 defines in its back, in the edges on both sides of it, locking recess 44 (see FIGS. 7 and 10) which widens backward in a V-shaped fashion in its cross section. In the rear of the locking recess 44, there is placed a locking member 46, which is in the shape of a bar which is thicker than the width of the through groove 42 and thinner than the locking recess 44. The surface of the locking member 46 is roughened by giving axial fine notches in them.

The locking member 46 is fixed at its base to one end of an arm 48. The arm 48 is journaled at the other end on the sliding block 36 in such a manner that it can pivot in a horizontal plane about a vertical axis, and, further, it is biased backward in such a manner that the locking member 46 is moved away from the locking recess 44 by a spring installed around a shaft on which the arm is journaled (the shaft cannot be seen in the Figures, shielded within the sliding block). Further, an indentation 50 is defined in the sliding block 36 on the edge of the locking recess, so that the arm may avoid interference with the edge as the arm 48 moves forward into the locking recess 44. Thus, the locking member 46, though usually positioned in the rearward of the locking recess 44 by being biased with the spring, can be fit in the locking recess 44 when a forward external force is applied to it.

Figure 11:
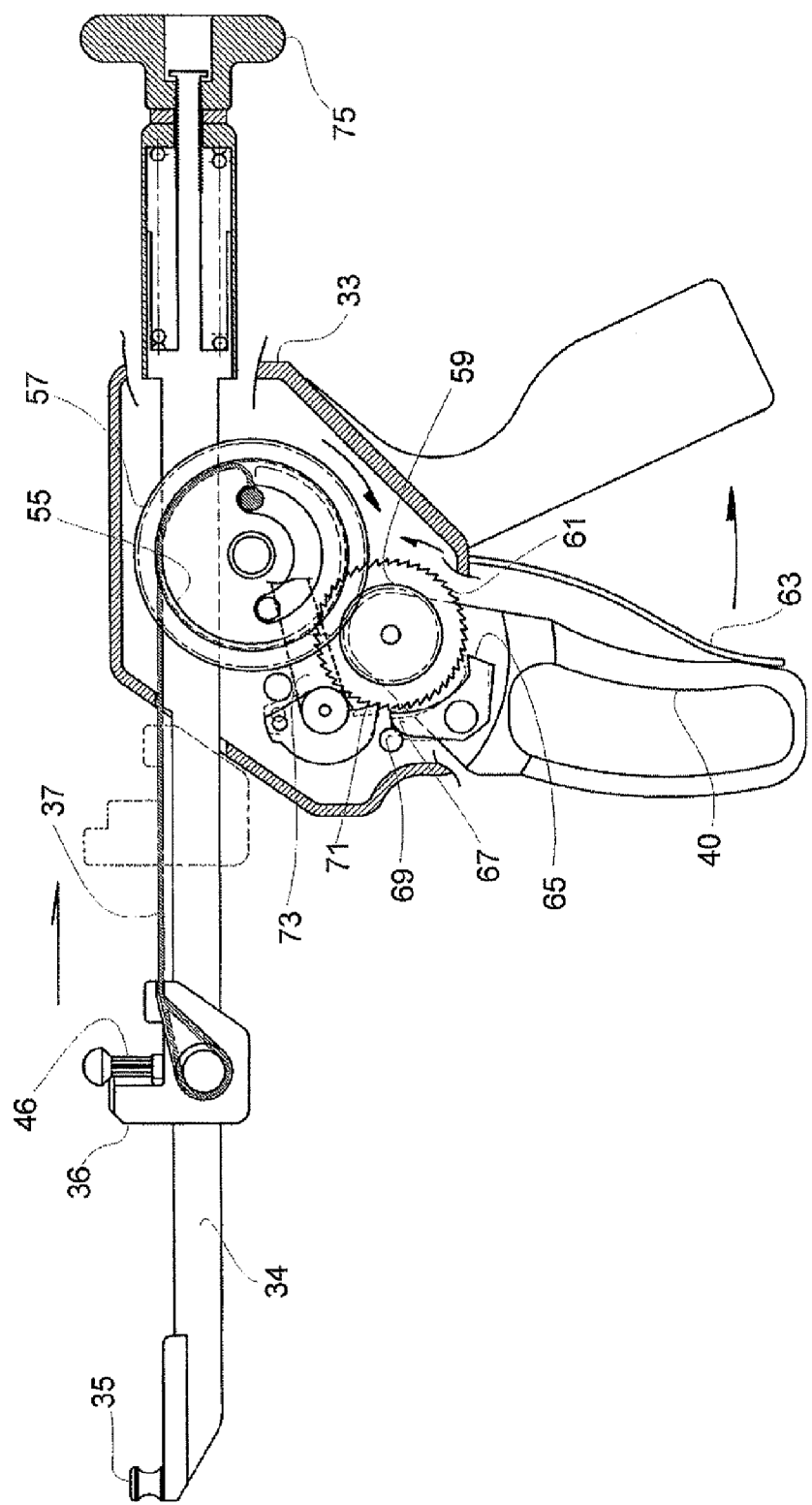
FIG. 11 illustrates a side sectional view of the device of Example 1.

FIG. 11 illustrates a side sectional view showing in general the internal structure of the device. In the figure, the pull cable 37 is secured at its rear end to the rotary drum 55 and is stretched along the surface of the drum. The rotary drum 55 has a gear 57 which is integral and concentric with the drum, with the gear 57 engaging with another gear 59. The gear 59 is concentric and integral with a ratchet wheel 61. The operation lever 40, which is secured to the very shaft to which the ratchet wheel 61 also is secured, has at its lower end a leaf spring 63 attached at its lower end. The leaf spring 63 then is fixed at its upper end to the housing of the grip portion 33, with the operation lever 40 being biased in the forward direction. The operation lever 40 is pivotally provided with a feed pawl 65, with the tip of it being biased toward the ratchet wheel 61. The other end 67 of the feed pawl 65 abuts on the pin 69 fixed on the housing of the grip portion 33, and thus a cam mechanism is formed by which when the operation lever 40 rests in its forward position, the feed pawl 65 is pivoted clockwise in the figure, thereby moving the tip of it away from the ratchet wheel 61. The ratchet wheel 61 is engaged by a spring-biased one-way detent 71. The one-way detent 71 is connected to the shaft of the release lever 73 placed outside of the grip portion 33. Thus, when the release lever 73 is pulled down, the one-way detent 71 gets out of engagement with the ratchet wheel 61 and allows the ratchet wheel 61, and therefore the gears 59, 57 and the rotary drum 55 also, to rotate in reverse direction, thus releasing the pull cable 37 from its tension.

Figure 12:
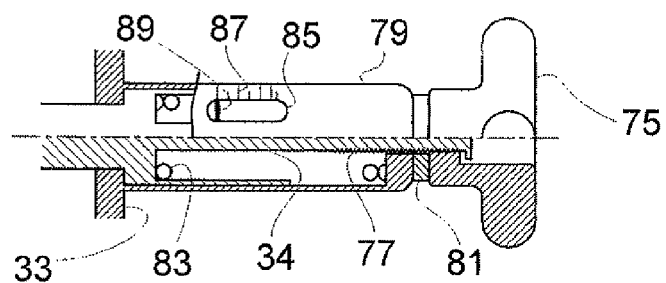
FIG. 12 is a schematic diagram showing the structure of the tension-adjusting mechanism.

FIG. 12 is a schematic diagram showing the structure of the device's tension-adjusting mechanism used for adjusting the tension of the cable to a desired level as bones are firmly tied with the bone-tying cable. In the figure, "75" indicates a tension-adjusting knob. The tension-adjusting knob 75 is provided with a female screw, which engages a male screw 77 formed at the rear end of the rod-like member 34. The rear end of the rod-like member 34 fits, slidably in the longitudinal direction, in a cylindrical member 79 which is combined with the housing of the grip portion 33 into one body, and the tension adjusting knob 75 abuts, with an intervening spacer 81 made of a material with a low coefficient of sliding friction, at the rear end of the cylindrical member 79. A coil spring 83 is inserted between the rear end of the is rod-like member 34 and the inner surface of the rear wall of the cylindrical member 79. When the tension-adjusting knob 75 is rotated clockwise, the rear end of the rod-like member 34, which is in screw-engagement with the knob, is drawn backward in accordance with the amount of rotation and retreat, thereby compressing the coil spring 83. Therefore, the more the amount of rotation of the tension-adjusting knob 75 is, the more compressed the coil spring 83 becomes, and the greater accumulation of repulsive force results in the spring. The cylindrical member 79 has a window 85, and around the edges of the window 85 are provided scale marks 87 which correspond to the strength of the tension. A bar 89, which is seen through the window 85 of the cylindrical member 79, is marked near the rear end of the rod-like member 34.

Figure 3:
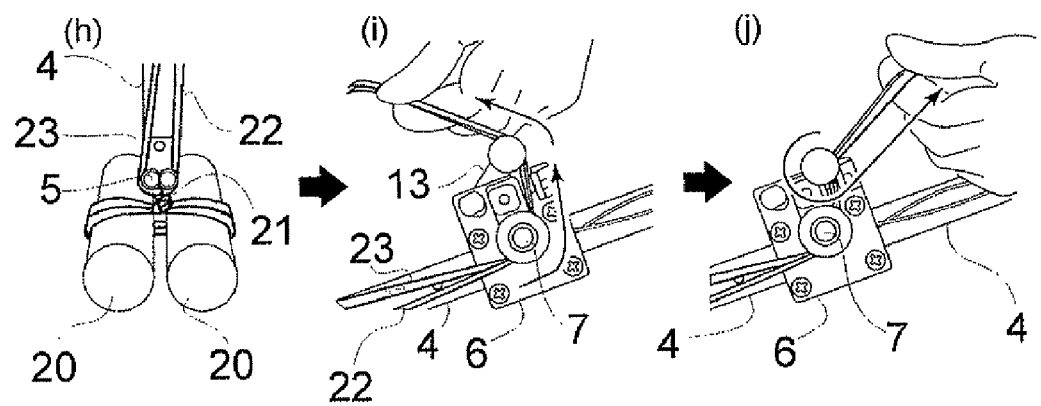
FIG. 3 is a schematic diagram showing the procedure of tying bones firmly using a conventional bone-tying cable tightening device.
Figure 4:
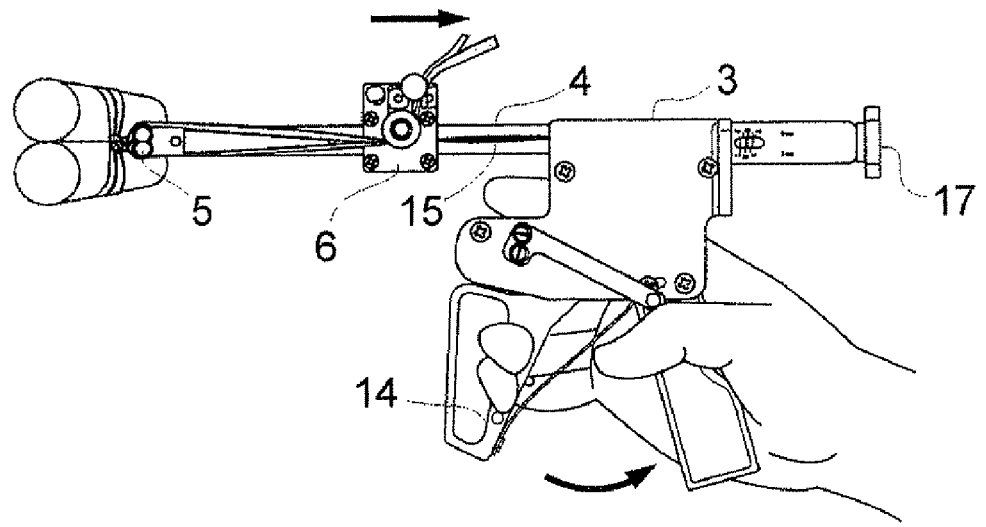
FIG. 4 is a schematic diagram showing the procedure of tying bones firmly using a conventional bone-tying cable tightening device.
Figure 5:
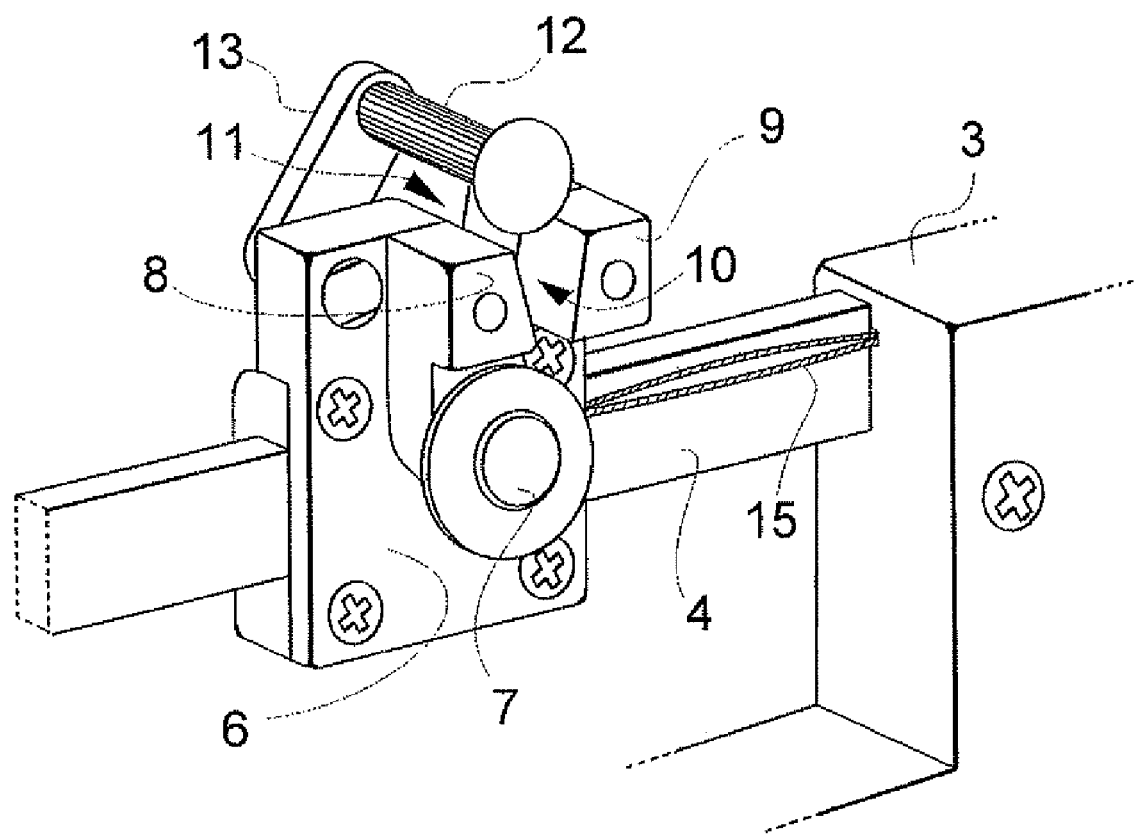
FIG. 5 illustrates an enlarged partial view of a conventional bone-tying cable tightening device, viewed obliquely from front.
Figure 6:
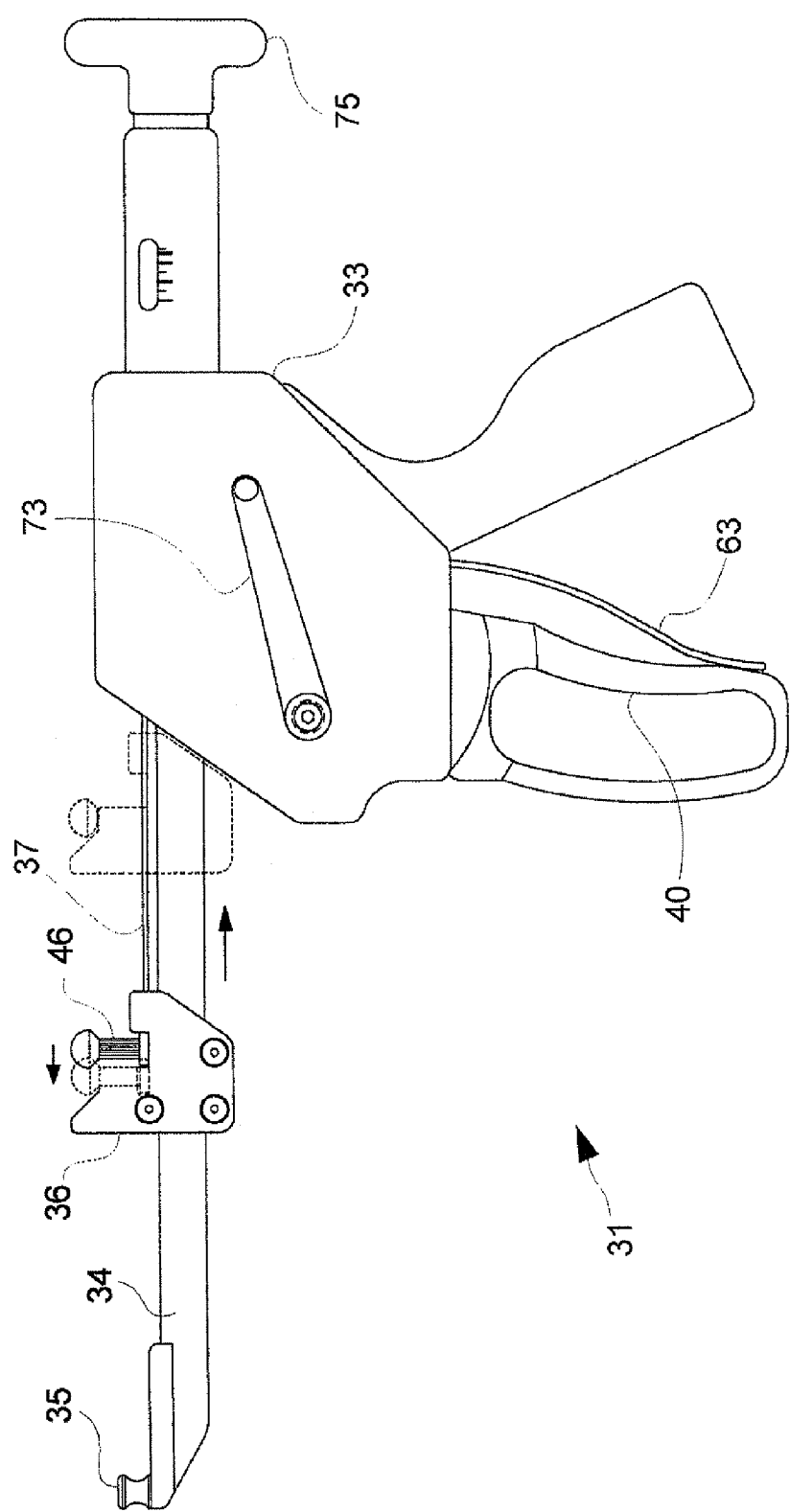
FIG. 6 illustrates a side view of the bone-tying cable tightening device of Example 1 of the present invention.
Figure 7:
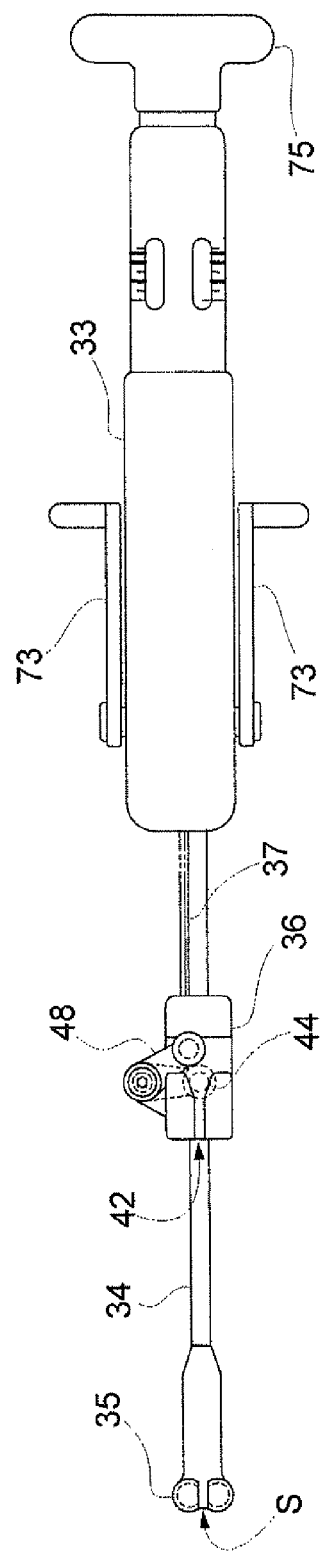
FIG. 7 illustrates a plan view of the device of Example 1.
Figure 8:
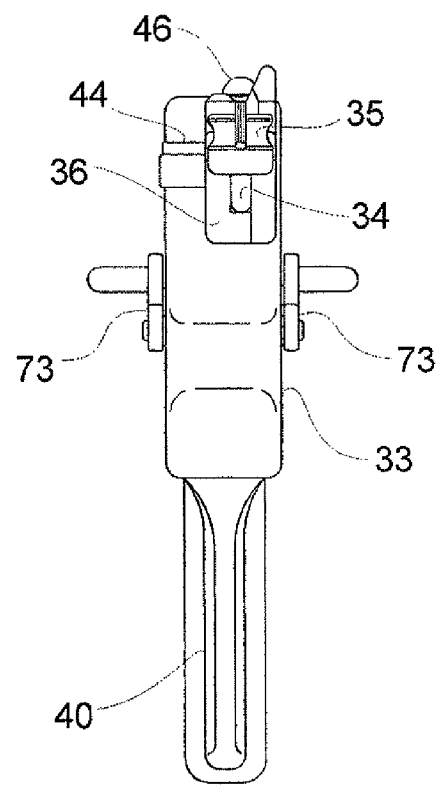
FIG. 8 illustrates a front view of the device of Example 1.
Figure 9:
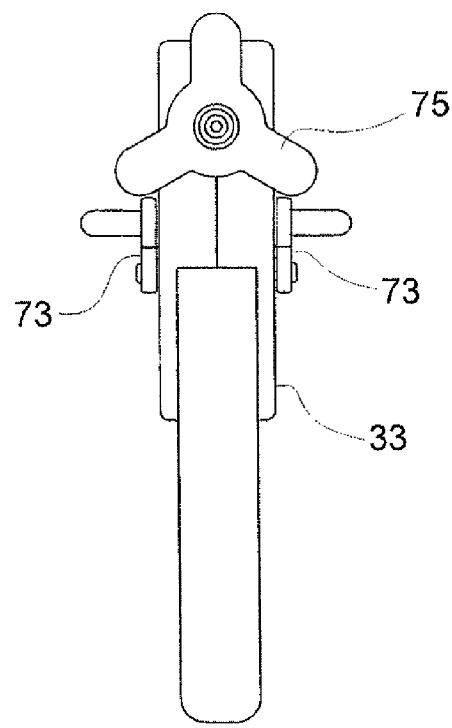
FIG. 9 illustrates a back view of the device of Example 1.
Figure 10:
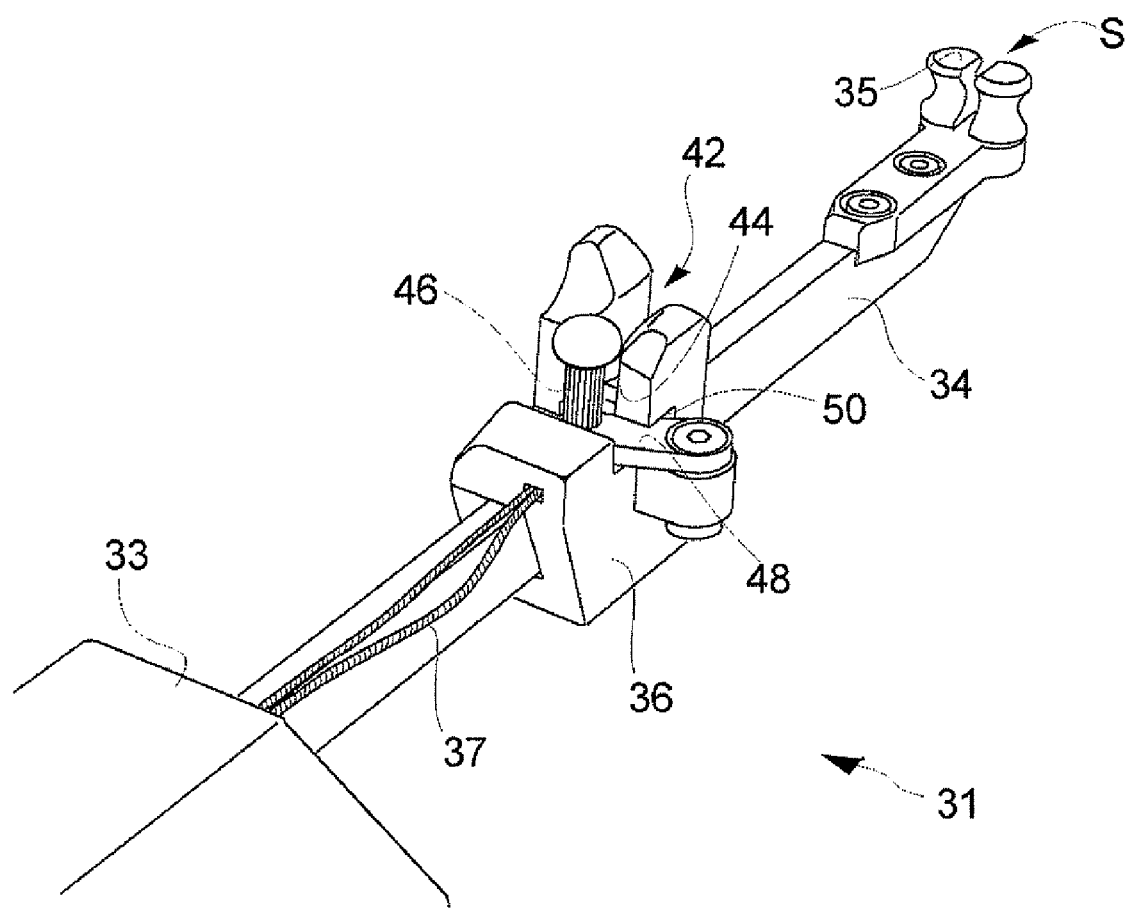
FIG. 10 illustrates an enlarged partial view of the device of Example 1, viewed obliquely from behind.
Figure 13:
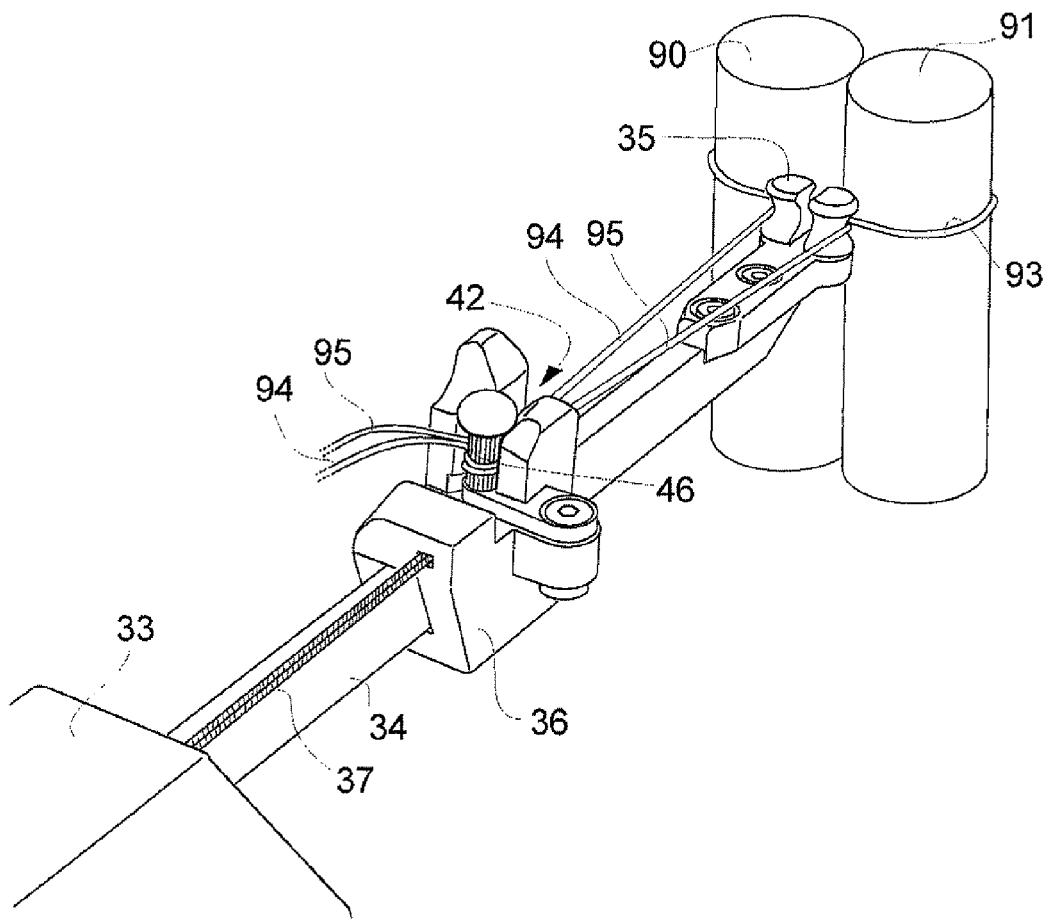
FIG. 13 illustrates an enlarged partial view of the device of Example 1 viewed, obliquely from behind, when bones are being tied firmly by it.

FIG. 13 is an enlarged partial view of the device of this example viewed obliquely from behind as two bones are being firmly tied by it. In the figure, "93" indicates a loop of a bone-tying cable with which the bones 90, 91, are being fastened, and "94" and "95" indicate two arms extending from a provisional knot (not seen behind the a projections 35) of the bone-tying cable. The procedure of forming a provisional knot is the same as has been described with reference to FIGS. 1 and 3 regarding a conventional device. The two arms 94, 95 of the bone-tying cable are separated away from each other, rightward and leftward, respectively, relative to the projections 35, then pulled backward, with the provisional knot being supported by the projections 35, and the both arms are passed through the through groove 42 as a bundle. Then they are wound once about the locking member 46, and the operation lever 40 is pulled a few times to make the sliding block 36 retreat. As a result, the two arms 94, 95 of the bone-tying cable becomes tense between the locking member 46 and the projections 35, and the locking member 46 about which they are wound is forced to fit in the locking recess 44. While the operation lever 40 is repeatedly pulled from this situation, causing the sliding block 36 to further retreat, the tension of the two arms 94, 95 of the bone-tying cable elevated between the locking member 46 and the projections 35 makes the locking member 46 fit tightly in the V-shaped locking recess 44, clamping with greater force the two arms 94, 95 of the bone-tying cable between it and the locking recess 44. Thus, as a result of increasing frictional force between them, the two arms 94, 95 of the bone-tying cable are tightly secured in place. Instead of separating the two arms 94, 95 of the bone-tying cable to both sides of the projections 35, it is also allowed to pull them backward through the slit S between the projections.

Figure 14:
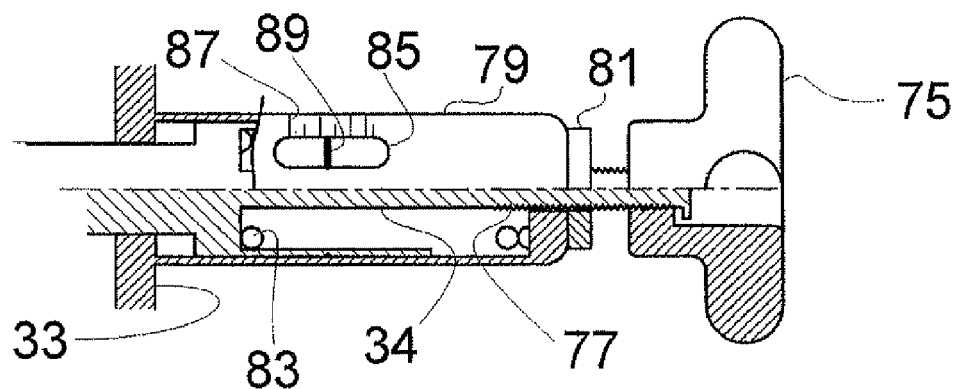
FIG. 14 is a schematic diagram showing the performance of the tension-adjusting mechanism.

As further repeated pulling of the operation lever 40 causes further retreat of the sliding block 36, thereby increasing the tension of the two arms 94, 95 of the cable, the cable mutually slips between its contact surfaces within the provisional knot. This makes the loop 93, shrink in its size gradually and firmly tie the bones 90, 92 at increasing strength. Throughout this process, though the rod-like member 34 also is pulled backward at the projection 35 by the pull cable via the locking member 46 and the sliding block 36, it continues to stay at is original position, since it is biased forward at its rear end by the coil spring 83, as far as the strength of the bias is not overcome by the backward pull. Now with reference to FIG. 14, at the moment when the tension of the loop 93 fastening the bones 90, 91 reaches a predetermined strength, and the pulling force just slightly exceeds a predetermined value which is correlated to the strength, the rod-like member 34 slightly retreat backward. This retreat is detectable either as a retreat of the tension-adjusting knob 75 or as a shift of the bar 89 seen through the window 85 of the cylindrical member 79. Therefore, the surgeon can know that the predetermined strength of tension has been achieved, when the rod-like member 34 has shifted slightly backward from its original position.

Thus, once the predetermined tension has been achieved, the release lever 73 is pulled down to disengage the one-way detent 71 from the teeth of the ratchet wheel 61, thereby releasing the ratchet mechanism. As the sliding block 36, therefore, is now released from the backward pull, the locking member 46 also is released from its engagement with the locking recess 44, and thus the two arms of the bone-tying cable can be removed from the locking member 46. The process using the device now is over, and then the knot is fixed, as done in conventional processes, by adding excess knots or by application of an adhesive, or the like.

Example 2

Figure 15:
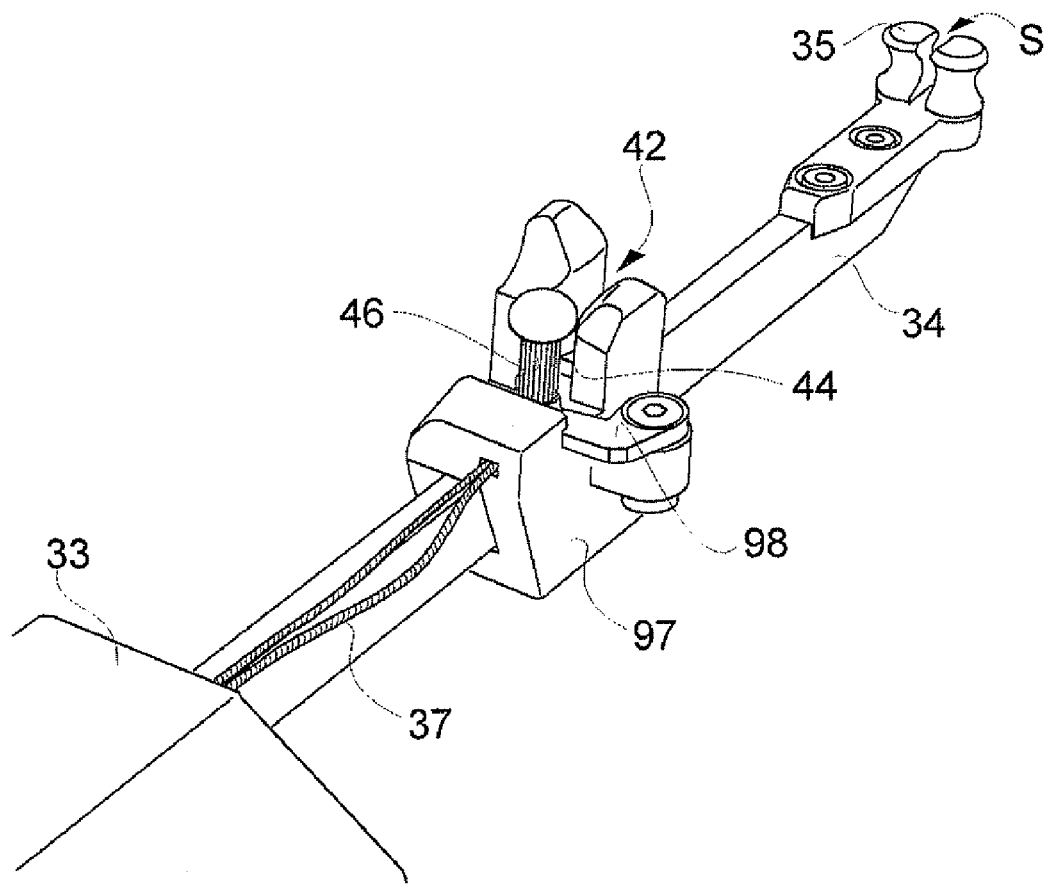
FIG. 15 illustrates an enlarged partial view of the bone-tying cable tightening device of Example 2 of the present invention, viewed obliquely from behind.

FIG. 15 illustrates an enlarged partial view of another example of the present invention, viewed obliquely from behind. In the figure, the same numerals as those seen in Example 1 indicate the parts corresponding to the latter. In the present example, the arm 98 installed pivotably on the sliding block 97 is formed in a shape of hook, and because of its contour thus formed as receding on its inner side, interference of the arm with the edge of the locking recess 44 is avoided when the arm pivots forward. In other aspects, the structure, function and manner of handling are as described in connection to Example 1.

Example 3

Figure 16:
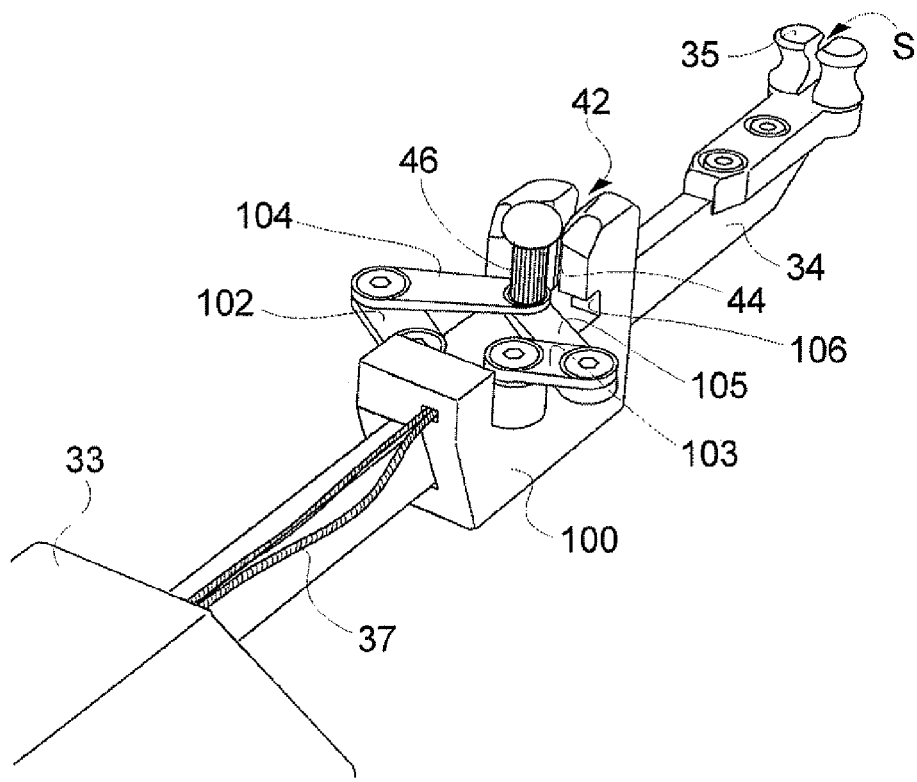
FIG. 16 illustrates an enlarged partial view of the bone-tying cable tightening device of Example 3 of the present invention, viewed obliquely from behind.

FIG. 16 illustrates an enlarged partial view of still another example of the present invention, viewed obliquely from behind. In the figure, the same numerals as those seen in Example 1 indicate the parts corresponding to the latter. In the present example, the sliding block 100 is provided with a pair of first arms 102, 103 which pivotably extend diagonally in lateral directions from both lateral sides of the sliding block, as well as a pair of second arms 104, 105 pivotably extending diagonally in inward directions from the tips of the first arms. And the tips of the second arms 104, 105 being connected pivotably with each other, a five-chain link is thus formed consisting of the sliding block 100, the pair of first arms 102, 103, and the pair of second arms 104, 105. At the tips of the pair of second arms is fixed a locking member 46. The pair of first arms 102, 103 are journaled on the sliding block 100, and biased so as to turn in rearward directions, respectively, by springs installed around their pivotal axes. In order to avoid interference that could occur when the second arms 104, 105 move forward, the sliding block 100 defines indentations 106 in the edges of the locking recess 44. Thus, the locking member 46, which is usually away rearward from the locking recess 44, can proceed linearly to fit in the locking recess 44 when a forward external force is applied to it. In other aspects, the structure, function and manner of handling are as described in connection to Example 1.

Example 4

Figure 17:
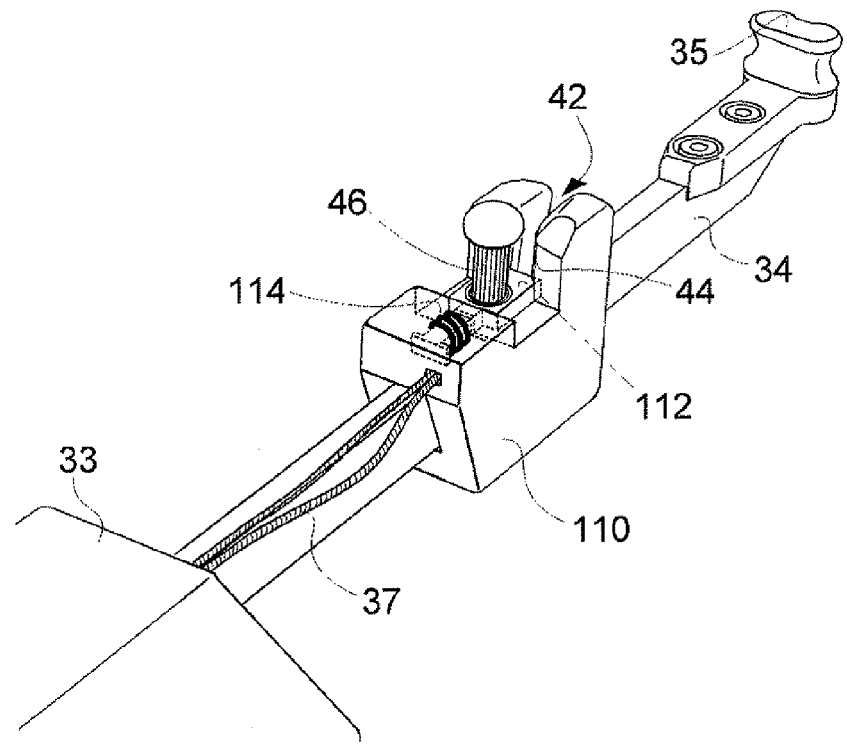
FIG. 17 illustrates an enlarged partial view of the bone-tying cable tightening device of Example 4 of the present invention, viewed obliquely from behind.

FIG. 17 illustrates an enlarged partial view of still another example of the present invention, viewed obliquely from behind. In the figure, the same numerals as those seen in Example 1 indicate the parts corresponding to the latter. In the present example, the sliding block 110 has a basal plate 112, which is mounted on it slidably in the longitudinal direction and is biased backward by a coil spring 114 confined in the rear of it, and the locking member 46 is fixed on the basal plate 112. Thus the locking member 46, which is usually away rearward from the locking recess 44, can proceed linearly to fit in the locking recess 44 when a forward external force is applied to it. In other aspects, the structure, function and manner of handling are as described in connection to Example 1. It is to be noted that, in the present example, the projection 35 is of a single-body structure, in contrast to those in Examples 1-3.

Example 5

Figure 18:
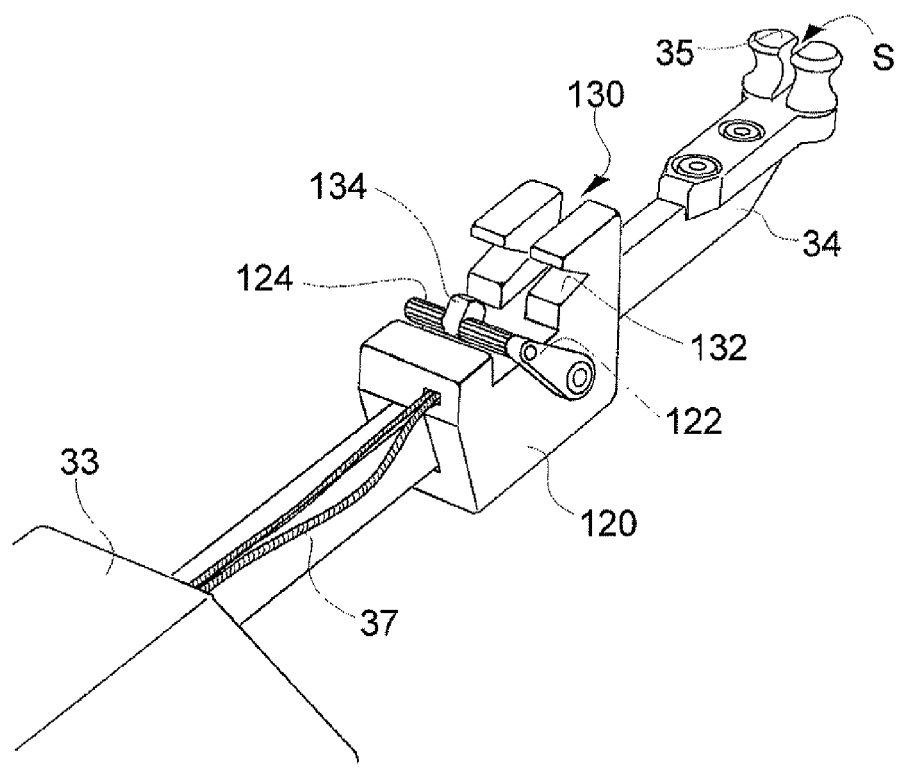
FIG. 18 illustrates an enlarged partial view of the bone-tying cable tightening device of Example 5 of the present invention, viewed obliquely from behind.

FIG. 18 illustrates an enlarged partial view of still another example of the present invention, viewed obliquely from behind. In the figure, the same numerals as those seen in Example 1 indicate the parts corresponding to the latter. In the present invention, an arm 122 is pivotably attached to the sliding block 120 on one of its lateral sides and extends generally upward while slanting backward, and at the tip of the arm is fixed a locking member 124 which extends inward over the sliding block 120. The arm 122 is biased backward by a spring inside the sliding block 120. A through groove 130 is defined in the sliding block 120, and a V-shaped locking recess 132 extends transversing the rear end of the through groove, intersecting the cross section of it. Thus the locking member 124, which is usually away rearward from the locking recess 132, can proceed to fit in the locking recess 132 when a forward external force is applied to it. The projection 134 in the center of the locking member 124 is a structure for preventing the two arms of the bone-tying cable from being wound exclusively right above the through groove 130, and it is of a width which can just fit in the through groove 130. In other aspects, the structure, function and manner of handling are as described in connection to Example 1.

Example 6

Figure 19:
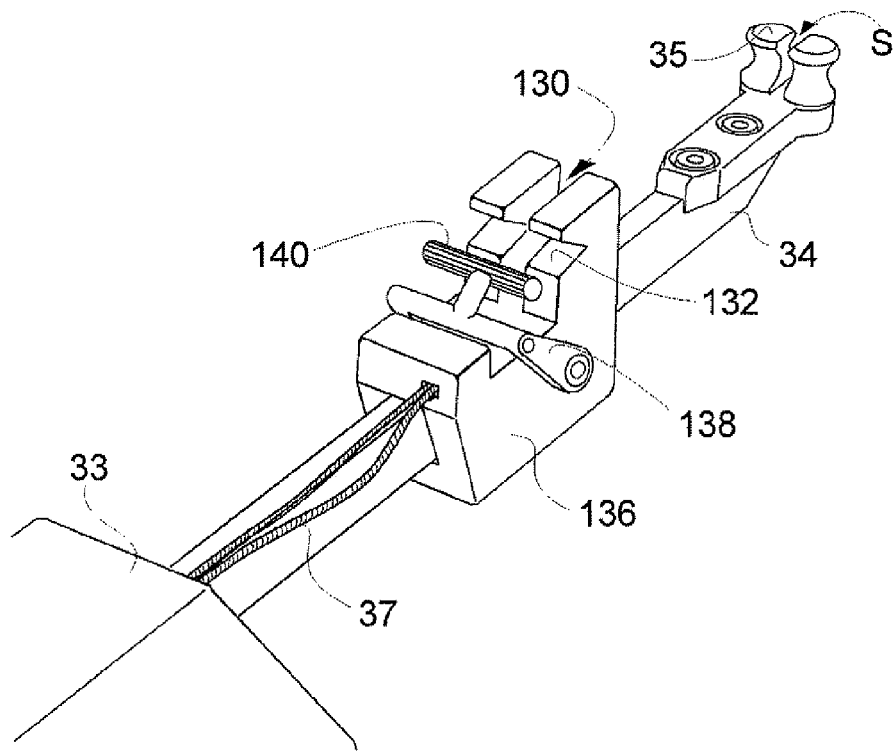
FIG. 19 illustrates an enlarged partial view of the bone-tying cable tightening device of Example 6 of the present invention, viewed obliquely from behind.

FIG. 19 illustrates an enlarged partial view of still another example of the present invention, viewed obliquely from behind. In the figure, the same numerals as those seen in Example 1 indicate the parts corresponding to the latter. In this example, an arm 138 which is pivotably attached to the sliding block 136 on its both lateral sides extends generally upward while slanting backward, and then, after extending inward above the sliding block to unite into one body in the middle, further extends generally upward while slanting forward, and at the tip of the arm thus formed is attached a locking member 140. The arm 138 is biased backward by a spring inside the sliding block 136. A through groove 130 is defined in the sliding block 136, and a V-shaped locking recess 132 extends transversing the rear end of the through groove, intersecting the cross section of it. Thus the locking member 140, which is usually away rearward from the locking recess 132, can proceed to fit in the locking recess 132 when a forward external force is applied to it. In other aspects, the structure, function and manner of handling are as described in connection to Example 1.

Example 7

Figure 20:
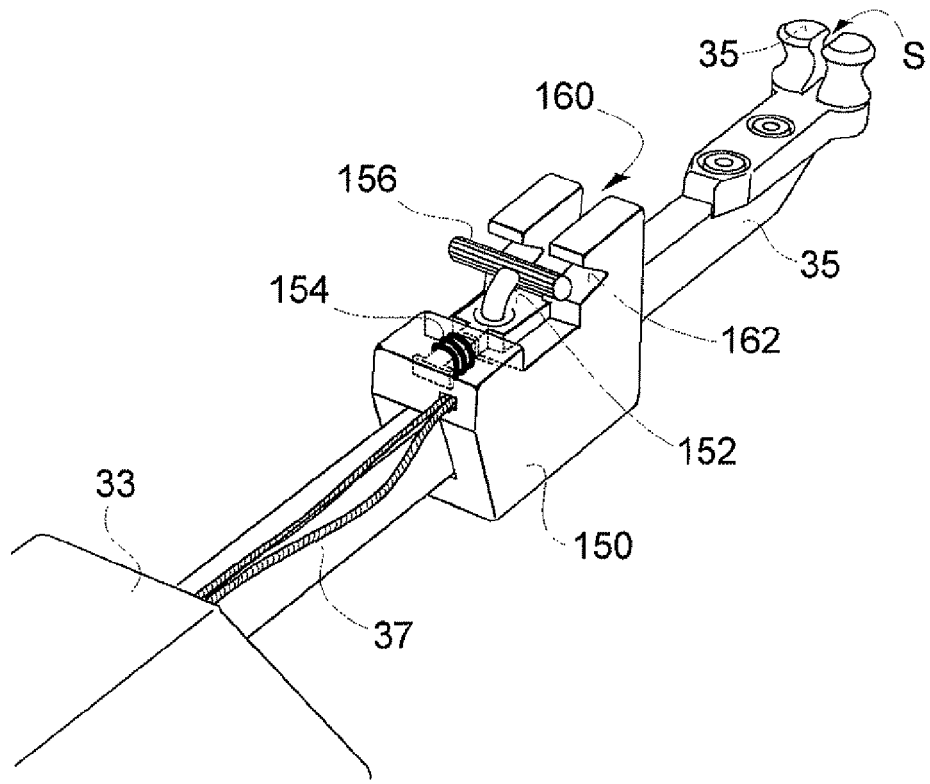
FIG. 20 illustrates an enlarged partial view of the bone-tying cable tightening device of Example 7 of the present invention, viewed obliquely from behind.

FIG. 20 illustrates an enlarged partial view of a still another example of the present invention, viewed obliquely from behind. In the figure, the same numerals as those seen in Example 1 indicate the parts corresponding to the latter. In the present example, the sliding block 150 has a basal plate 152, which is mounted on it slidably in the longitudinal direction and is biased backward by a coil spring 154 confined in the rear of it, and the locking member 156 is fixed on the basal plate 152. A through groove 160 is defined in the sliding block 150, and a V-shaped locking recess 162 extends transversing the rear end of the through groove, intersecting the cross section of it. Thus the locking member 156, which is usually away rearward from the locking recess 44, can linearly proceed to fit in the locking recess 44 when a forward external force is applied to it. In other aspects, the structure, function and manner of handling are as described in connection to Example 1.

Example 8

Figure 21:
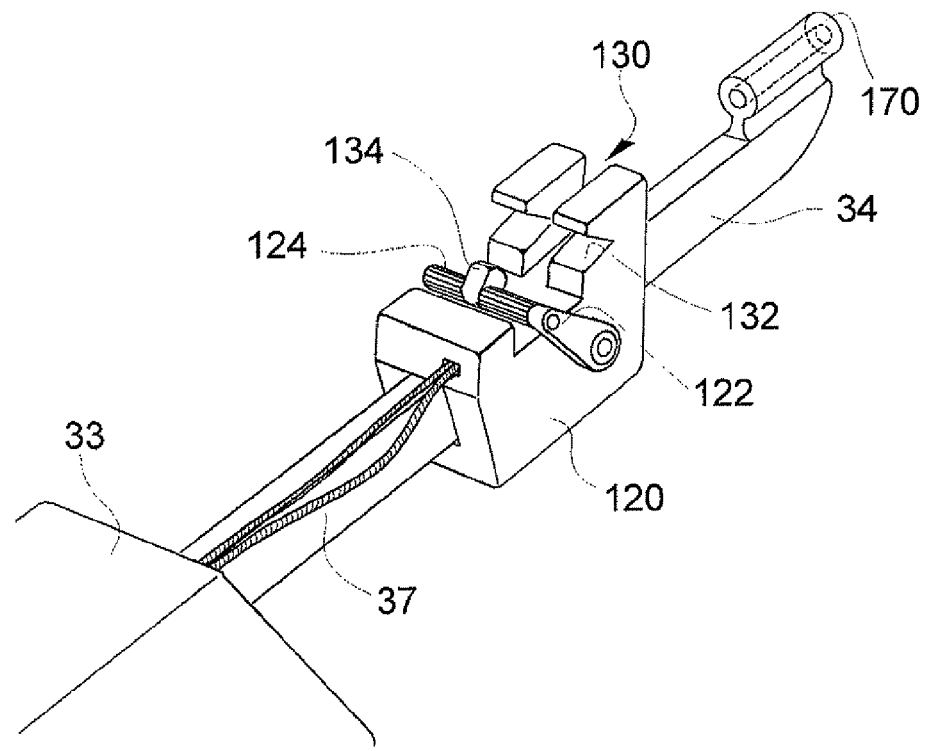
FIG. 21 illustrates an enlarged partial view of the bone-tying cable tightening device of Example 8 of the present invention, viewed obliquely from behind.

FIG. 21 illustrates an enlarged partial view of still another example of the present invention, viewed obliquely from behind. The present example is the same as Example 5, except that the former is provided with a cylindrical member 170, instead of the projections 35. The cylindrical member 170 is used to support at its tip the provisional knot, with the two arm of the cable being passed through its bore. While it will be easy in the case where the cable is made of metal fiber, in order to pass a cable through the bore when it is made of synthetic fibers, such a cable is chosen as having at either end a structure (e.g., a loop of a string) to which a wire can be hooked, and the cable then is passed using a wire hooked to the structures as a guide.

INDUSTRIAL APPLICABILITY

According to the present invention, during the process of leading the two arms of a bone-tying cable held together to the locking member, there is no more need for turning the cable in the lateral direction, and the transverse load is thus eliminated which otherwise is applied during the operation for winding the cable. And improvement is also achieved during the operation regarding simultaneous visibility of the tip of the device and the locking member. Therefore, the present invention provides a bone-tying cable tightening device which is made easier to handle for the process up to winding of the cable about the locking member.

The invention claimed is:

1. A bone-tying cable tightening device for firmly tying objects to be tied, by pulling two arms extending from a knot of a cable tying the objects to be tied, comprising:
    a grip portion to be held with a hand,
    a rod-like member which extends forward from the grip portion,
    a knot-supporting means provided at the tip of the rod-like member to support the knot when the two arms are pulled,
    a sliding block mounted around the rod-like member in a longitudinally slidable fashion, which sliding block is provided with a cable-holding means to grip and hold the two arms together and is connected, via a tension transmitter means, to a pulling means installed in the grip portion, and
    an operation lever provided in the grip portion to drive the pulling means, wherein
    the knot-supporting means is of a structure which defines, above the rod-like member,
    (1) supporting faces on both sides thereof of which the two arms can be hooked away from each other and laterally relative to the longitudinal axis of the rod-like member, and/or
    (2) a slit or bore through which the two arms can be passed, and
    wherein the cable-holding means connected to the sliding block comprises
    (a) a longitudinal through groove defined in the upper part of the sliding block,
    (b) a locking recess which extends, at the rear end of the through groove, either transversing the through groove in the cross section thereof or including the cross section of the through groove along the central axis thereof, and whose width in the cross section thereof widens in the rearward direction,
    (c) a backward biased locking member about which the two arms are to be wound, and which is provided movably back and forth behind the locking recess on the upper side of the sliding block and so made that the forward movement thereof is blocked when it proceeds in the locking recess and abuts, with the side faces thereof, on the same.

2. The bone-tying cable tightening device of claim 1, wherein the locking recess extends covering the cross section of the through groove along the central axis thereof.

3. The bone-tying cable tightening device of claim 2, wherein the locking member is attached to an arm which is installed, pivotably about a vertical axis, on the sliding block and on the same side as the knot-supporting means relative to the rod-like member.

4. The bone-tying cable tightening device of claim 3, wherein the locking recess defines in the edge thereof an indentation which can accommodate the arm as the locking member fits in the locking recess.

5. The bone-tying cable tightening device of claim 3, wherein the arm has a contour which evades the edge of the locking recess so that the arm may avoid interference with the edge of the locking recess as the locking member fits in the locking recess.

6. The bone-tying cable tightening device of claim 3, wherein the arm is journaled on the sliding block.

7. The bone-tying cable tightening device of claim 6, wherein the backward bias of the locking member is given by a spring installed around the pivotal shaft of the arm journaled on the sliding block.

8. The bone-tying cable tightening device of claim 2, wherein the locking member is installed at the tips of a second arms of a five-link chain mechanism comprising:
   a pair of first lateral arms of equal length which are installed, on the same side as the knot-supporting means relative to the rod-like member, pivotably about vertical axes on both lateral sides of the sliding block and extending diagonally in lateral directions, respectively, and
   a pair of second lateral arms of equal length which are attached, pivotably about vertical axes, to one or the other of the pair of first lateral arms at the tips thereof, and extends diagonally in inward directions therefrom, respectively, the tips of the pair of second arms being connected pivotably with each other about a vertical axis.

9. The bone-tying cable tightening device of claim 8, wherein the pair of first arms are journaled on the sliding block.

10. The bone-tying cable tightening device of claim 9, wherein the backward bias of the locking member is given by a spring installed around at least one of the pivotal shafts of the pair of first arms journaled on the sliding block.

11. The bone-tying cable tightening device of claim 2, wherein the locking member is installed on a sliding member which is mounted on, and slidably back and forth relative to, the sliding block.

12. The bone-tying cable tightening device of claim 11, wherein the sliding member slides along a sliding guide formed in the sliding block and to which part of the sliding member fits.

13. The bone-tying cable tightening device of claim 12, wherein the backward bias of the locking member is given by a spring installed in the sliding guide in association with the sliding member.

14. The bone-tying cable tightening device of claim 1, wherein the locking recess extends transversing the through groove in the cross section thereof.

15. The bone-tying cable tightening device of claim 14, wherein the locking member is mounted on an arm which is installed, pivotably about a horizontal axis, on a lateral side of the sliding block.

16. The bone-tying cable tightening device of claim 15, wherein the arm extends generally in the upward direction from the lateral side of the sliding block, and the locking member extends from the tip of the arm, in the rear of the locking recess and in parallel to the same.

17. The bone-tying cable tightening device of claim 15, wherein the arm extends generally in the upward direction separately from the both lateral sides of the sliding block, respectively, and then inward above the sliding block to unite into one body, and again generally in the upward direction, and at the tip of the arm the locking member is attached.

18. The bone-tying cable tightening device of claim 15, wherein the arm is journaled on the sliding block.

19. The bone-tying cable tightening device of claim 18, wherein the backward bias of the locking member is given by a spring installed around a pivotal shaft of the arm journaled on the sliding block.

20. The bone-tying cable tightening device of claim 14, wherein the locking member is installed on a sliding member which is mounted on the sliding block, slidably back and forth relative thereto.

21. The bone-tying cable tightening device of claim 20, wherein the sliding member slides along a sliding guide which is formed in the sliding block and to which part of the sliding member fits.

22. The bone-tying cable tightening device of claim 21, wherein the backward bias of the locking member is given by a spring installed in the sliding guide in association with the sliding member.

23. The bone-tying cable tightening device of claim 1, wherein the width of the locking recess in the cross section thereof widens in a V-shaped fashion in the rearward direction.

24. The bone-tying cable tightening device of claim 1, wherein the width of the locking recess in the cross section thereof widens in a circular arc-like fashion in the rearward direction.

25. A bone-tying cable tightening device for firmly tying objects to be tied, by pulling two arms extending from a knot of a cable tying the objects to be tied, comprising:
   a grip portion to be held with a hand,
   a rod-like member which extends forward from the grip portion,
   a knot-supporter provided at the tip of the rod-like member capable of supporting the knot when the two arms are pulled,
   a sliding block mounted around the rod-like member in a longitudinally slidable fashion, which sliding block is provided with a cable-holder capable of griping and holding the two arms together and is connected, via a tension transmitter, to a puller installed in the grip portion, and
   an operation lever provided in the grip portion to drive the pulling means, wherein
   the knot-supporter is of a structure which defines, above the rod-like member,
   (1) supporting faces on both sides thereof of which the two arms can be hooked away from each other and laterally relative to the longitudinal axis of the rod-like member, and/or
   (2) a slit or bore through which the two arms can be passed, and
   wherein the cable-holder connected to the sliding block comprises
   (a) a longitudinal through groove defined in the upper part of the sliding block,
   (b) a locking recess which extends, at the rear end of the through groove, either transversing the through groove in the cross section thereof or including the cross section of the through groove along the central axis thereof, and whose width in the cross section thereof widens in the rearward direction,
   (c) a backward biased locking member about which the two arms are to be wound, and which is provided movably back and forth behind the locking recess on the upper side of the sliding block and so made that the forward movement thereof is blocked when it proceeds in the locking recess and abuts.

26. The bone-tying cable tightening device of claim 25, wherein the locking member is attached to an arm which is installed, pivotably about a vertical axis, on the sliding block and on the same side as the knot-supporter relative to the rod-like member.

* * * * *